US00PP28663P2

(12) United States Plant Patent
Thompson Trust

(10) Patent No.: US PP28,663 P2
(45) Date of Patent: Nov. 21, 2017

(54) JAPANESE HASKAP PLANT NAMED 'CHITO'

(50) Latin Name: ***Lonicera caerulea* ssp. *emphyllocalyx***
Varietal Denomination: Chito

(71) Applicant: Maxine M. Thompson Trust, Corvallis, OR (US)

(72) Inventor: Maxine M. Thompson Trust, Corvallis, OR (US)

(73) Assignee: MAXINE M. THOMPSON TRUST, Corvallis, OR (US)

( * ) Notice: Subject to any disclaimer, the term of this patent is extended or adjusted under 35 U.S.C. 154(b) by 39 days.

(21) Appl. No.: 14/757,022

(22) Filed: Nov. 9, 2015

(51) Int. Cl.
*A01H 5/08* (2006.01)

(52) U.S. Cl.
USPC ..... Plt./156

(58) Field of Classification Search
USPC ..... Plt./156
See application file for complete search history.

*Primary Examiner* — Keith Robinson
(74) *Attorney, Agent, or Firm* — Penny J. Aguirre

(57) ABSTRACT

A new cultivar of Japanese haskap plant, 'Chito', that is characterized by its slightly open growth habit that allows excellent presentation of the fruit, its consistently high fruit yields, fruits that are ornamental, large, oval-ovate in shape, and light blue in color with a tart/sweet flavor, and its medium strong fruit attachment to the stem that is strong enough to prevent pre-harvest drop and loose enough to permit easy picking without tearing the fruit flesh.

2 Drawing Sheets

Botanical classification: *Lonicera caerulea* ssp. *emphyllocalyx*.

Variety denomination: 'Chito'.

CROSS REFERENCE TO RELATED APPLICATIONS

This application is co-pending with U.S. Plant Patent Applications filed for plants derived from the same breeding program that are entitled Japanese haskap Plant Named 'Kapu' U.S. Plant Pat. No. 26,820 and Japanese haskap Plant Named 'Taka' U.S. Plant Pat. No. 26,707.

BACKGROUND OF THE INVENTION

The present invention relates to a new and distinct cultivar of *Lonicera caerulea* ssp. *emphyllocalyx* and will be referred to hereafter by its cultivar name, 'Chito'. 'Chito' is a new cultivar of Japanese blue honeysuckle berry, also known as Japanese haskap, a plant grown for its fruit that is marketed as fresh fruit, frozen fruit and processed food products.

The new Invention arose from an ongoing controlled breeding program in Corvallis, Oreg. that commenced with the planting of seeds collected in 2000 from several berry farms in Hokkaido, Japan. The objectives of the breeding program are to develop superior cultivars of this early ripening berry plant that could be grown in moderate to colder climates combined with an upright spreading plant habit and fruit that were large in size, firm, easy to pick, good tasting, and with a high yield rate.

This new Japanese haskap cultivar, 'Chito', arose from seed collected from open pollination of an unnamed Japanese haskap plant that was growing on a farm near Chitose, Hokkaido, Japan. 'Chito' was selected in Corvallis, Oreg. as a single unique plant in 2004 from the population of resulting seedlings.

Asexual propagation of the new cultivar was first accomplished by the Inventor by hardwood stem cuttings in 2004 in Corvallis, Oreg. Asexual propagation by hardwood and softwood cuttings has determined that the characteristics of the new cultivar are stable and are reproduced true to type in successive generations.

SUMMARY OF THE INVENTION

The following traits have been repeatedly observed and represent the characteristics of the new cultivar as grown outdoors in a trial plot in Corvallis, Oreg. These attributes in combination distinguish 'Chito' as a unique cultivar of Japanese haskap.

1. 'Chito' exhibits a slightly open growth habit that allows excellent presentation of the fruit.
2. 'Chito' exhibits consistently high fruit yields.
3. 'Chito' exhibits fruits that are ornamental, large, oval-ovate in shape, and light blue in color with a tart/sweet flavor.
4. 'Chito' exhibits a medium strong fruit attachment to the stem that is strong enough to prevent pre-harvest drop and loose enough to permit easy picking without tearing the fruit flesh.

The Inventor has no records on the characteristics of the female parent as data was not recorded at that time. 'Chito' can be most closely compared to Japanese haskap cultivars 'Kapu' and 'Taka'. 'Kapu' is similar to 'Chito' in having a similar fruit flavor. 'Kapu' differs from 'Chito' in having a very upright growth habit with denser branching, in having fruit that is firmer and matures about one week later. 'Taka' is similar to 'Chito' in having a similar blooming period and fruit harvest date. 'Taka' differs from 'Chito' in having fruit that is cylindrical in shape, slightly sweeter in flavor and slightly firmer.

BRIEF DESCRIPTION OF THE DRAWINGS

The accompanying colored photographs were taken in mid summer and illustrate the overall appearance and distinct characteristics of 10 year-old plants of the new Japanese haskap as grown in a trial garden in Corvallis, Oreg.

The photograph in FIG. 1 provides a view of the plant habit of 'Chito'.

Figure 1:
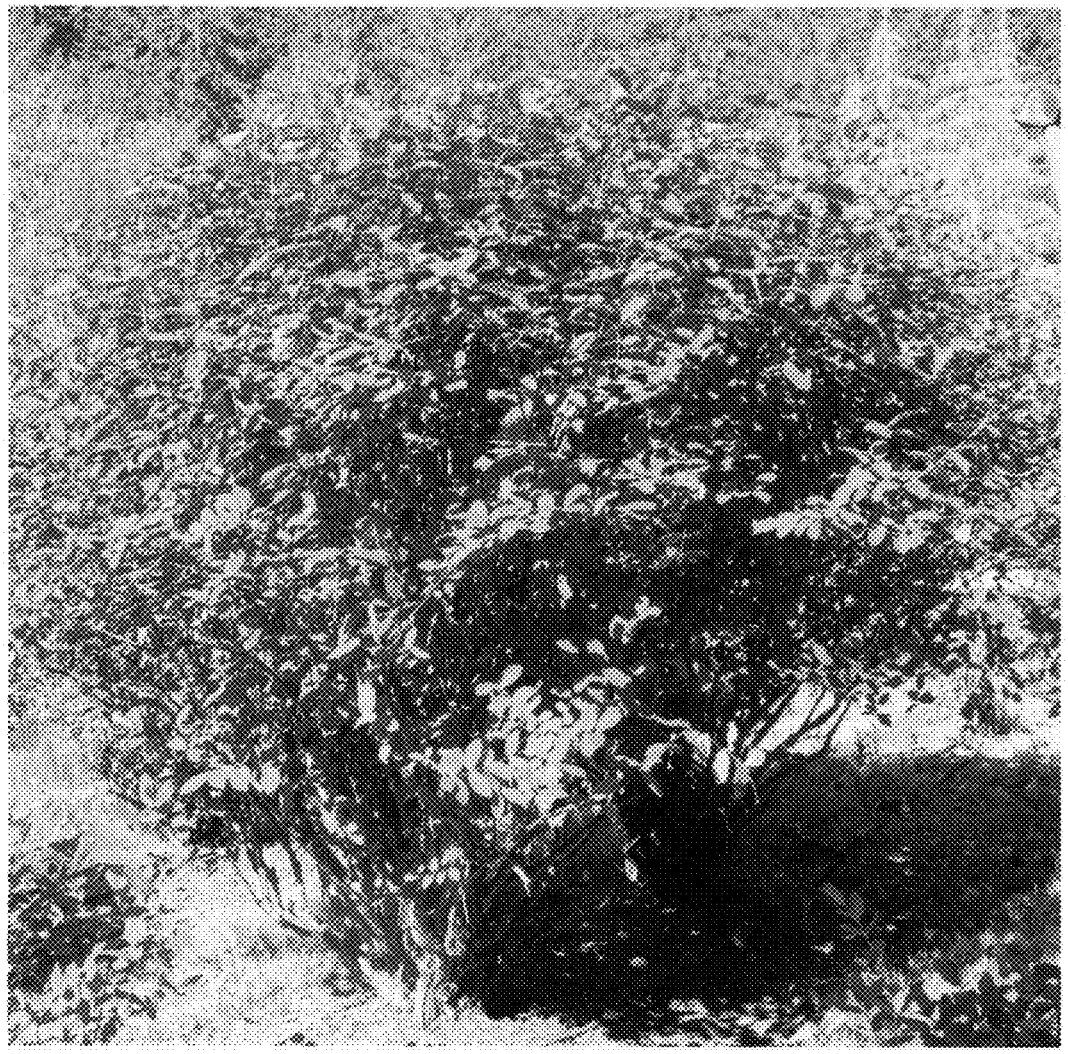
Figure 2:
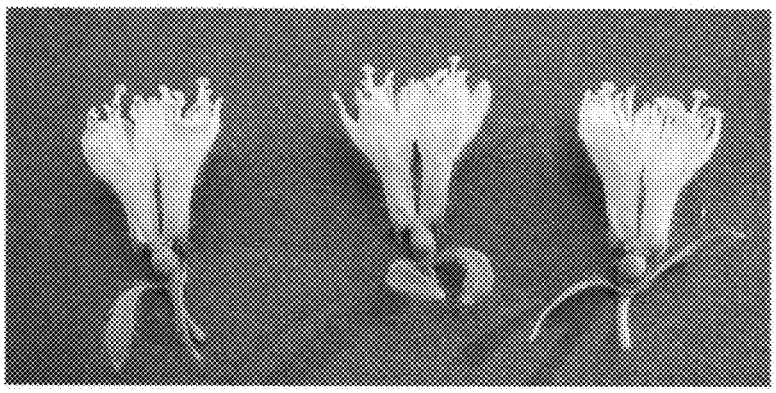

The photograph in FIG. 2 provides a close-up view of the flowers of 'Chito'.

Figure 3:
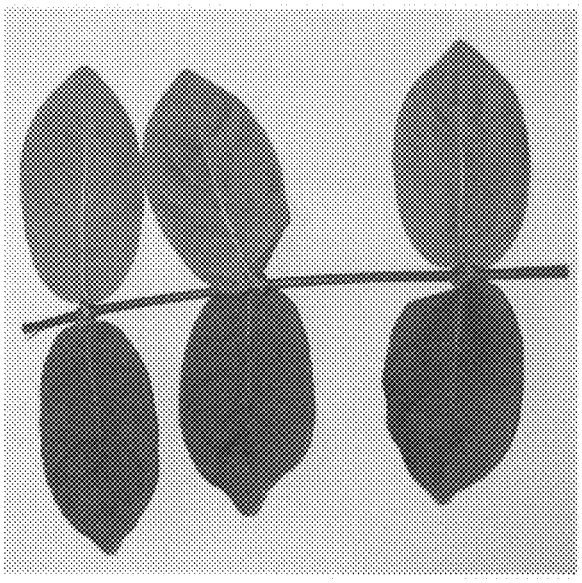

The photograph in FIG. 3 provides a close-up view of the leaves of 'Chito'.

Figure 4:
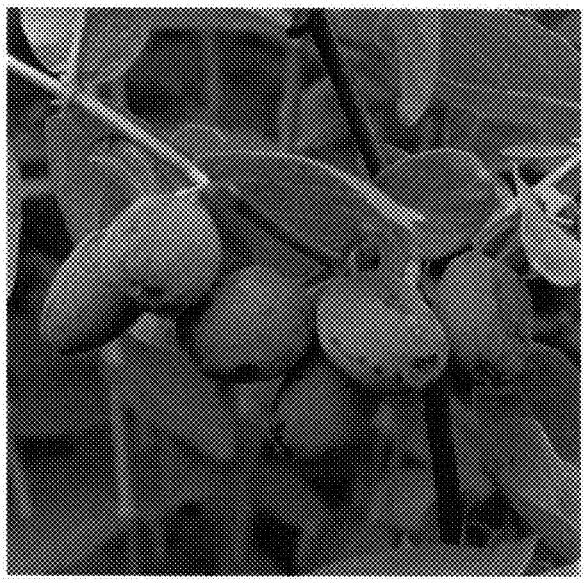

The photograph in FIG. 4 provides a view of the berries of 'Chito'.

The colors in the photographs may differ slightly from the color values cited in the detailed botanical description, which accurately describe the colors of the new Japanese haskap.

DETAILED BOTANICAL DESCRIPTION

The following is a detailed description of 10 year-old plants of the new Japanese haskap as field grown at the Inventor's farm in Corvallis, Oreg. under irrigation. The phenotype of the new cultivar may vary with variations in environmental, climatic, and cultural conditions, as it has not been tested under all possible environmental conditions. The color determination is in accordance with The 1995 R.H.S. Colour Chart of The Royal Horticultural Society, London, England, except where general color terms of ordinary dictionary significance are used.

General description:

*Plant type*.—Deciduous shrub, fruit bearing.

*Plant habit*.—Somewhat open, spreading.

*Plant size*.—Reaches an average of 2 m in height and 1.7 m in width.

*Hardiness*.—Adapted well in Zone 8b, expected to be hardy to U.S.D.A. Zone 4 but they have not been tested to date.

*Diseases and pests*.—No significant diseases or pest problems have been observed to date.

*Root description*.—Fibrous.

*Propagation*.—Softwood and hardwood stem cuttings.

*Growth rate*.—Vigorous.

*Root development*.—10 days to initiate roots in summer at 26° C., and 35 days to produce a fully rooted cutting or a young rooted plant in a liner at 26° C.

Dormant shoots:

*Density*.—Somewhat open.

*New growth*.—138C in color, and glabrous surface.

*One year-old shoots*.—55 cm in length and 4 mm in diameter, surface is smooth and glabrous, lenticels absent, 177A in color; adventitious bud development: medium, dormant without pruning, average of 2 per node, up to 2.5 mm in length and 2 mm in width, ovate in shape, a blend of 165A and 165B in color.

*Three year-old stems*.—1.24 m in length and 1.4 cm in diameter, surface exfoliating, inner bark 173C in color, outer bark 197A in color.

*Bud break*.—Early March in Corvallis, Oreg.

Foliage description:

*Leaf shape*.—Oval.

*Leaf division*.—Simple.

*Leaf base*.—Slightly cordate.

*Leaf apex*.—Obtuse.

*Leaf venation*.—Pinnate, color primarily matches leaf color on both surfaces.

*Leaf margins*.—Entire, setulose.

*Leaf arrangement*.—Opposite.

*Leaf attachment*.—Petiolate.

*Leaf surface*.—Young leaf and mature leaves, upper and lower surfaces are glabrous.

*Leaf internode length*.—An average of 4.6 cm.

*Leaf size*.—Average of 6.9 cm in length and 4 cm in width.

*Leaf color*.—Young leaves; upper surface 138A and lower surface 138B, mature leaves; upper surface 138A, lower surface 138B.

*Petioles*.—Up to 1 mm in length and 1 mm in width, 145C in color, glabrous surface.

*Stipules*.—Absent.

Inflorescence description:

*Blooming period*.—An average of 22 days, typically from March 31st to April 24$^{th}$ with mid bloom around April 13$^{th}$ in Corvallis, Oreg.

*Inflorescence type*.—Small 2-flowered cymule born in leaf axils of lowest 1 to 4 nodes on current years' growth.

*Inflorescence size*.—An average of 2.2 cm in length, 1.7 cm diameter at apex and 5 mm at base.

*Flower buds*.—Mixed buds, flower buds are not visible as they are enclosed within the leaves.

*Flower fragrance*.—None.

*Lastingness of inflorescence*.—4 to 6 days.

*Flower quantity*.—2 to 6 per shoot.

*Flower type*.—Epigynous.

*Corolla form*.—Funnel form, narrow at the base and widening towards apex, 5-lobed.

*Flower size*.—Length from base of ovary to stigma is 2.2 cm; average of base width is 2 mm, average of apex is 8 mm.

*Peduncles*.—4 mm in length, 1 mm in diameter, 135C in color, glabrous surface.

*Pedicels*.—Inconspicuous.

*Bracts*.—2, present at the base of the ovaries, linear in shape, upper surface color is 135C, lower surface color is 135C, upper and lower surfaces are glabrous, cuspidate apex, cuneate base, 2 mm in width and 1 cm in length.

*Sepals*.—Fused with hypanthium, 4.5 mm in length.

*Petals*.—5, fused into tube with apex of each free forming lobes, 2 mm in width at the base, 8 mm in diameter at apex and tube is 1.5 cm in length, free portion length is 5 mm and 4 mm in width, obtuse in shape, color of inside and outside of tube is 18C, inner and outer surfaces are pilose.

Reproductive organs:

*Gynoecium*.—1 pistil, an average of 2.2 cm in length, style is 1.8 cm in length and 18C in color, stigma is 1 mm in diameter and 10C in color, ovary is inferior, oval in shape, 4 mm in length, 3 mm in width and 135C in color.

*Androcoecium*.—5 stamens, adnate to inner corolla tube, filaments are 18C in color and about 5 mm in length, anthers are 18A in color, pollen is abundant in quantity and 19A in color with 99% acetocarmine stain.

*Compatibility*.—Self-incompatible.

Fruit description:

*Fruit development*.—60 days from mid-bloom to harvest.

*Harvest date*.—Average of June 12$^{th}$ in Corvallis, Oreg.

*Fruit type*.—True berry, consists of 2 ovaries enclosed in the hypanthium.
*Fruit shape*.—Oval-ovate.
*Fruit size*.—An average of 1.9 cm in length and 1.3 cm in width.
*Fruit surface*.—Smooth with medium bloom.
*Fruit apex*.—Obtuse.
*Fruit skin color*.—99A with bloom removed, 97C with bloom.
*Fruit flesh color*.—139C.
*Fruit firmness*.—Medium.
*Fruit brix*.—13°.
*Fruit juiciness*.—Relatively low.
*Fruit weight*.—An average of 2 g.
*Fruit yield*.—3.8 kg per 10 year-old bush.
*Pediuncle-berry scar*.—Very small, dry, up to 1 cm in length.
*Fruit attachment strength*.—Medium; strong enough to avoid pre-harvest drop and loose enough to pick without tearing berry flesh.
*Pre-harvest drop*.—Significant if harvest is delayed.
*Post-harvest*.—Berries maintain their appearance, firmness and taste for at least 3 weeks in cold storage at 33° F. to 35° F.
*Market uses*.—Fresh, frozen, dried, and particularly suited for processed products.
*Seed*.—Average of 11 seeds per fruit, lenticular in shape, dry weight size is 158 mg/100 seeds, 174B in color.

It is claimed:

1. A new and distinct cultivar of Japanese haskap plant named 'Chito' as herein illustrated and described.

* * * * *